(12) United States Patent
Chang et al.

(10) Patent No.: US 10,059,659 B2
(45) Date of Patent: Aug. 28, 2018

(54) ENANTIOMERICALLY PURE BINAPHTHOL DERIVATIVES AND METHOD FOR PREPARING THE SAME

(75) Inventors: Rae Kyu Chang, Gyeonggi-do (KR); Yun Soo Ahn, Seoul (KR); Heejung Jung, Gyeonggi-do (KR); Hyerim Ga, Seoul (KR); Juwan Maeng, Gyeonggi-do (KR); Young-Kook Koh, Gyeonggi-do (KR); Young Hee Lee, Chungcheongbuk-do (KR); Kwang Jae Lee, Gyeonggi-do (KR); Joonseo Kim, Gyeonggi-do (KR); Hyunil Lee, Gyeonggi-do (KR); Heungsik Yoon, Gyeonggi-do (KR)

(73) Assignee: AMINOLOGICS CO. LTD., Seoul (KR)

(*) Notice: Subject to any disclaimer, the term of this patent is extended or adjusted under 35 U.S.C. 154(b) by 45 days.

(21) Appl. No.: 13/994,328

(22) PCT Filed: Dec. 13, 2011

(86) PCT No.: PCT/KR2011/009579
§ 371 (c)(1),
(2), (4) Date: Aug. 27, 2013

(87) PCT Pub. No.: WO2012/081885
PCT Pub. Date: Jun. 21, 2012

(65) Prior Publication Data
US 2014/0012038 A1    Jan. 9, 2014

(30) Foreign Application Priority Data
Dec. 16, 2010 (KR) .................. 10-2010-0129080

(51) Int. Cl.
*C07C 273/18* (2006.01)
*C07B 57/00* (2006.01)
*C07C 275/32* (2006.01)

(52) U.S. Cl.
CPC ........ *C07C 273/1854* (2013.01); *C07B 57/00* (2013.01); *C07C 275/32* (2013.01)

(58) Field of Classification Search
None
See application file for complete search history.

(56) References Cited

U.S. PATENT DOCUMENTS

| 6,849,742 B2 | 2/2005 | Ueno et al. |
| 7,268,252 B2 | 9/2007 | Kim et al. |
| 2006/0173211 A1* | 8/2006 | Kim et al. .................. 562/439 |

FOREIGN PATENT DOCUMENTS

| JP | 2006-213712 | 8/2006 |
| JP | 2009-23989 | 2/2009 |
| KR | 100661280 B1 | 8/2006 |
| WO | 2010055966 A1 | 5/2010 |

OTHER PUBLICATIONS

International Search Report for PCT/KR2011/009579, dated Jun. 29, 2012.
Hyunjung Park et al. "Chirality Conversion of Dipeptides in the Schiff Bases of Binol Aldehydes with Multiple Hydrogen Bond Donors", Bulletin of Korean Chemical Society, 2009, vol. 30, No. 2, pp. 409-414.
Lijun Tang et al. "Reactive Extraction of Enantiomers of 1,2-Amino Alcohols via Stereoselective Thermodynamic and Kinetic Processes", Journal of Organic Chemistry, 2008, 73, pp. 5996-5999.
Raju Nandhakumar et al. "Effects of ring substituents on enantioselective recognition of amino alcohols and acids in uryl-based binol receptors", 2008, Tetrahedron, 64, pp. 7704-7708.

* cited by examiner

*Primary Examiner* — Sudhakar Katakam
*Assistant Examiner* — Jennifer Sawyer
(74) *Attorney, Agent, or Firm* — Arent Fox LLP

(57) ABSTRACT

The present invention relates to compounds 1, 1a (S-enantiomer) and 1b (R-enantiomer) of the following formula 1, and a method for preparing the same. [formula 1] The novel compound of the formula 1 is used as an important intermediate for preparing compounds 6, 6a (S-enantiomer) and 6b (R-enantiomer) of the following formula 6, which are 2,2'-binaphthol-3-aldehyde derivatives. Also, the present invention provides a method for preparing the compound of formula 1 with a very safe method at low cost. [formula 6]

5 Claims, No Drawings

ENANTIOMERICALLY PURE BINAPHTHOL DERIVATIVES AND METHOD FOR PREPARING THE SAME

CROSS-REFERENCE TO RELATED APPLICATION

This application is a U.S. National Stage Application under 35 U.S.C. § 371 of International Patent Application No. PCT/KR2011/009579, filed Dec. 13, 2011, which claims benefit to Korean Application No. KR 10-2010-0129080, filed Dec. 16, 2010, the entirety of both applications are incorporated herein by reference.

TECHNICAL FIELD

The present invention relates to novel compounds used as an important intermediate in the method for preparing the compound of a 2,2'-binaphthol-3-aldehyde derivative and a method for preparing the same.

BACKGROUND ART

Compounds where the hydrogen of the 2' hydroxyl group in 2,2'-binaphthol-3-aldehyde is selectively substituted are used for various uses. Among such compounds, the compound of the following formula 6, which is very useful for separating chiral amino alcohols or amino acids into their respective optical isomers by recognizing their chirality through an imine bond or for converting L-amino acid into D-amino acid or D-amino acid into L-amino acid, has been developed by the inventors of the present invention and patented (Korean Patent No. 0661280).

[formula 6]

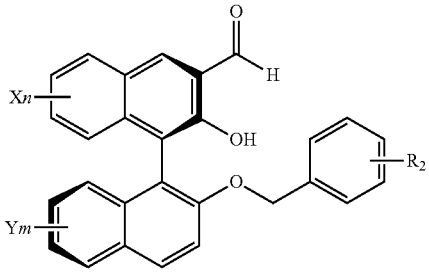

6

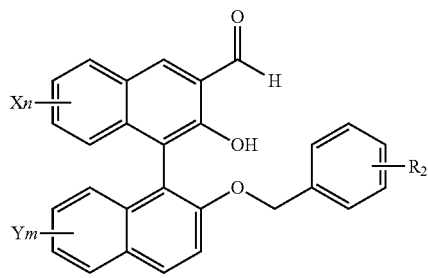

6a

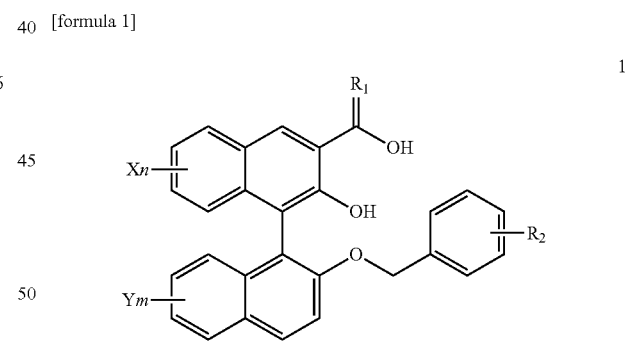

6b

However, according to the prior art where the hydrogen of the 2' hydroxyl group in 2,2'-binaphthol-3-aldehyde is substituted, a mixed product of a compound where the hydrogen of the 2 hydroxyl group is substituted and a compound where the hydrogen of the 2' hydroxyl group is substituted is obtained because of the low selectivity for the 2' hydroxyl group. In particular, compounds where the hydrogen of the 2 hydroxyl group is substituted are obtained in more amounts. Such mixed product has a problem that the efficiency for preparing the target product is greatly deteriorated because the mixture cannot be easily separated, and thus there is a difficulty such as that the alkylation process must be carried out after protecting the 2 hydroxyl group with a protecting group to achieve substitution of the hydrogen of the 2' hydroxyl group. Thus, a technology for increasing the selectivity for hydrogen of the 2' hydroxyl group, which prevents byproducts from being generated, is required.

Meanwhile, the novel compounds of the present invention, binaphthol derivatives, are represented by the following formula 1, and for the preparation of said compound, the compound of the following formula 2 can be used.

[formula 1]

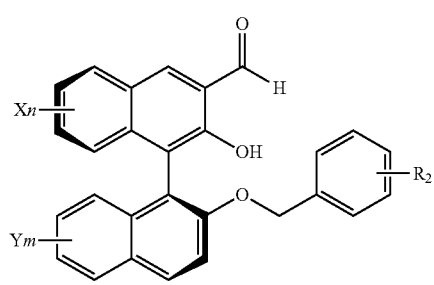

1

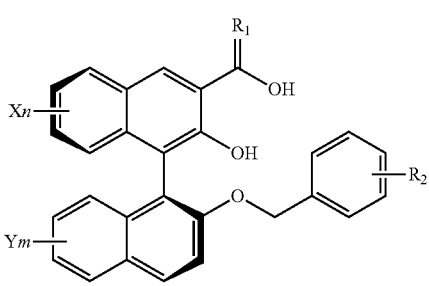

1a

-continued

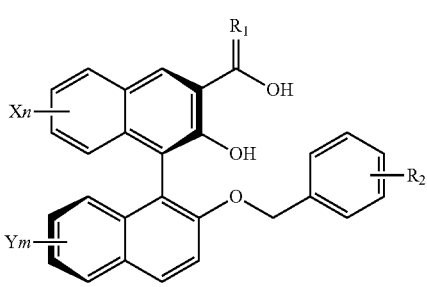

[formula 2]

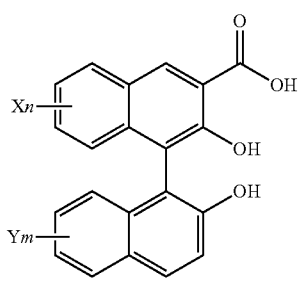

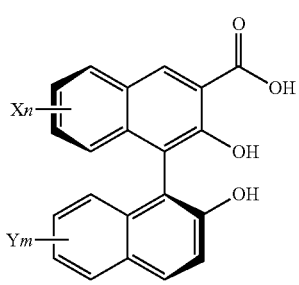

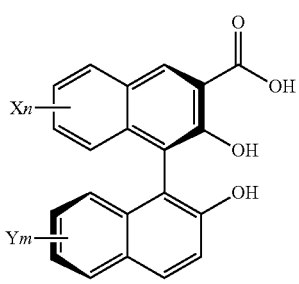

Also, the starting material used in prior art, enantiomerically pure binaphthol, is relatively expensive. Thus, it is necessary to develop a method for preparing enantiomerically pure binaphthol derivatives using cheaper materials.

DISCLOSURE OF INVENTION

Technical Problem

It is an object of the present invention to solve the above problems of prior art. Thus, it is an object of the present invention to provide novel compounds, binaphthol derivatives of formula 1, prepared by selectively introducing various substituents into the hydrogen position of the 2' hydroxyl group using the compound of formula 2, 2,2'-binaphthol-3-carboxylic acid, instead of using 2,2'-binaphthol-3-aldehyde.

Also, it is an object of the present invention to provide a method for preparing the binaphthol derivative of formula 1 economically by a safe method without using harmful materials.

Solution to Problem

The present invention provides compounds represented by the formula 1.

[formula 1]

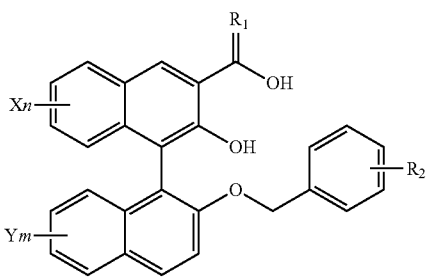

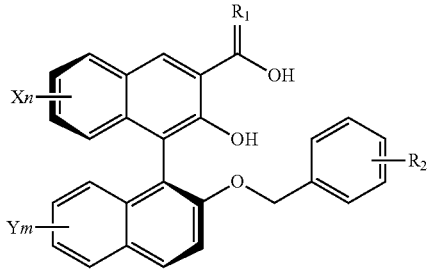

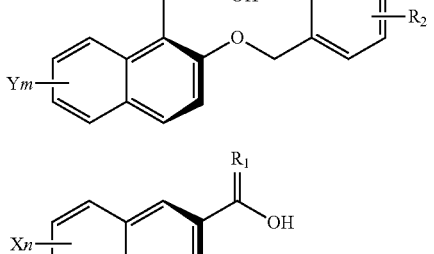

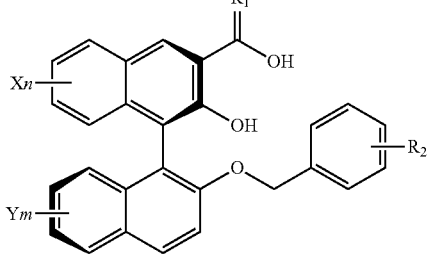

wherein X and Y are each independently selected from the group consisting of hydrogen; halogen; amino; nitro; cyano; $C_1$-$C_{10}$ alkyl non-substituted or substituted with at least one substituent selected from the group consisting of halogen, hydroxyl, amino, cyano, nitro and $C_6$-$C_{10}$ aryl; $C_1$-$C_{10}$ alkyl carbonyl; $C_5$-$C_{10}$ aryl; and $C_1$-$C_{10}$ alkoxy; n and m are each independently an integer from 0 to 5; $R_1$ is hydrogen or oxygen; and $R_2$ is —$NO_2$, —NH(NHBOCNBOC), —NHCX'$R_3$, —NHS(=O)$_a$$R_3$ or —NHPO(OH)$R_3$, wherein X' is oxygen or sulfur; a is 1 or 2; and $R_3$ is hydrogen; $C_1$-$C_{10}$ alkyl non-substituted or substituted with a halogen; —$NR_4R_5$; or $OR_6$, wherein $R_4$ to $R_6$ are each independently selected from the group consisting of hydrogen; $C_1$-$C_{10}$ alkyl non-substituted or substituted with a halogen; $C_5$-$C_{12}$ aryl non-substituted or substituted with at least one substituent selected from the group consisting of halogen, nitro, $C_1$-$C_5$ alkyl, $C_1$-$C_5$ alkoxy and $C_1$-$C_5$ perfluoroalkyl.

The present invention provides a method for preparing the compound represented by the formula 1, characterized by comprising the step of reacting the compound represented by the formula 2 with the compound represented by the formula 3 in the presence of a base.

[formula 2]

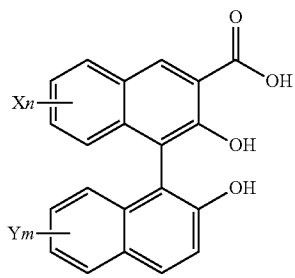

2

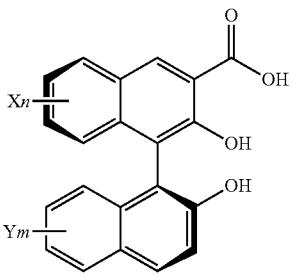

2a

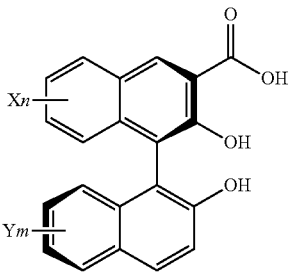

2b

[formula 3]

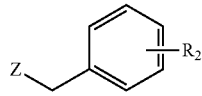

3 wherein X, Y, n, m and $R_2$ are each identical as defined above, and Z is halogen.

Advantageous Effects of Invention

In the case of using the compound of formula 2 of the present invention, various substituents can be introduced into the hydrogen position of the 2' hydroxyl group of the 2,2'-binaphthol-3-carboxylic acid very efficiently.

Also, the preparation method of the present invention provides a method for preparing binaphthol derivatives of formula 1 very safely and economically. Thus, the method can provide a great effect when applied to a production line of an industrial scale.

Mode for the Invention

The present invention relates to a compound of the following formula 1 and a method for preparing the same.

[formula 1]

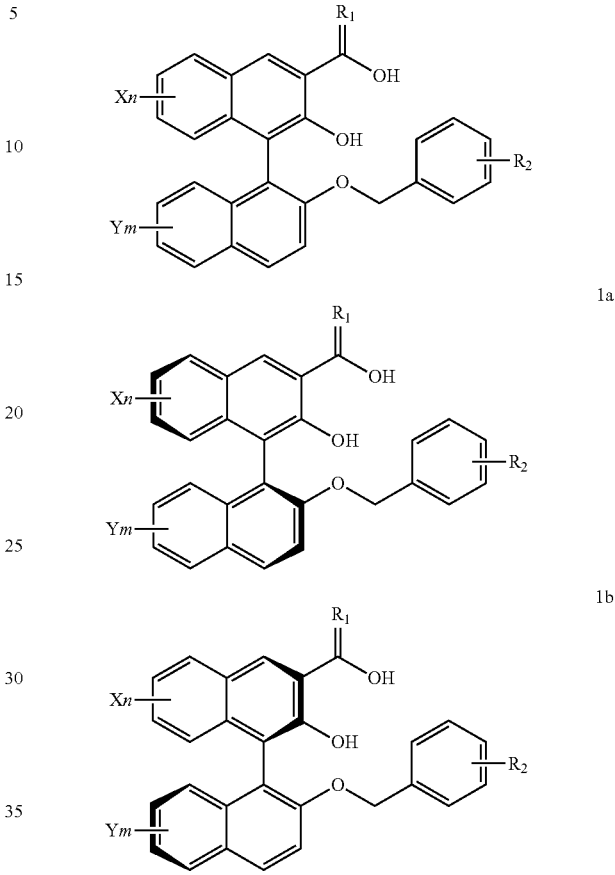

wherein X, Y, n, m, $R_1$ and $R_2$ are each as defined above.

The compound of formula 1 can be used as an important intermediate for preparing the compound of formula 6, which is a 2,2'-binaphthol-3-aldehyde derivative.

Also, the present invention provides a method for preparing compound 1 represented by formula 1, characterized by comprising the step of reacting the compound 2 represented by formula 2 with the compound 3 represented by formula 3 in the presence of a base.

The reaction formula of the above preparation method is represented as follows:

[Reaction formula 1]

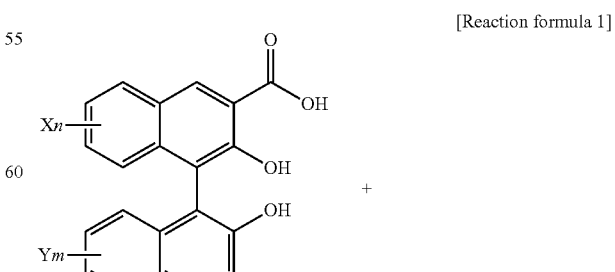

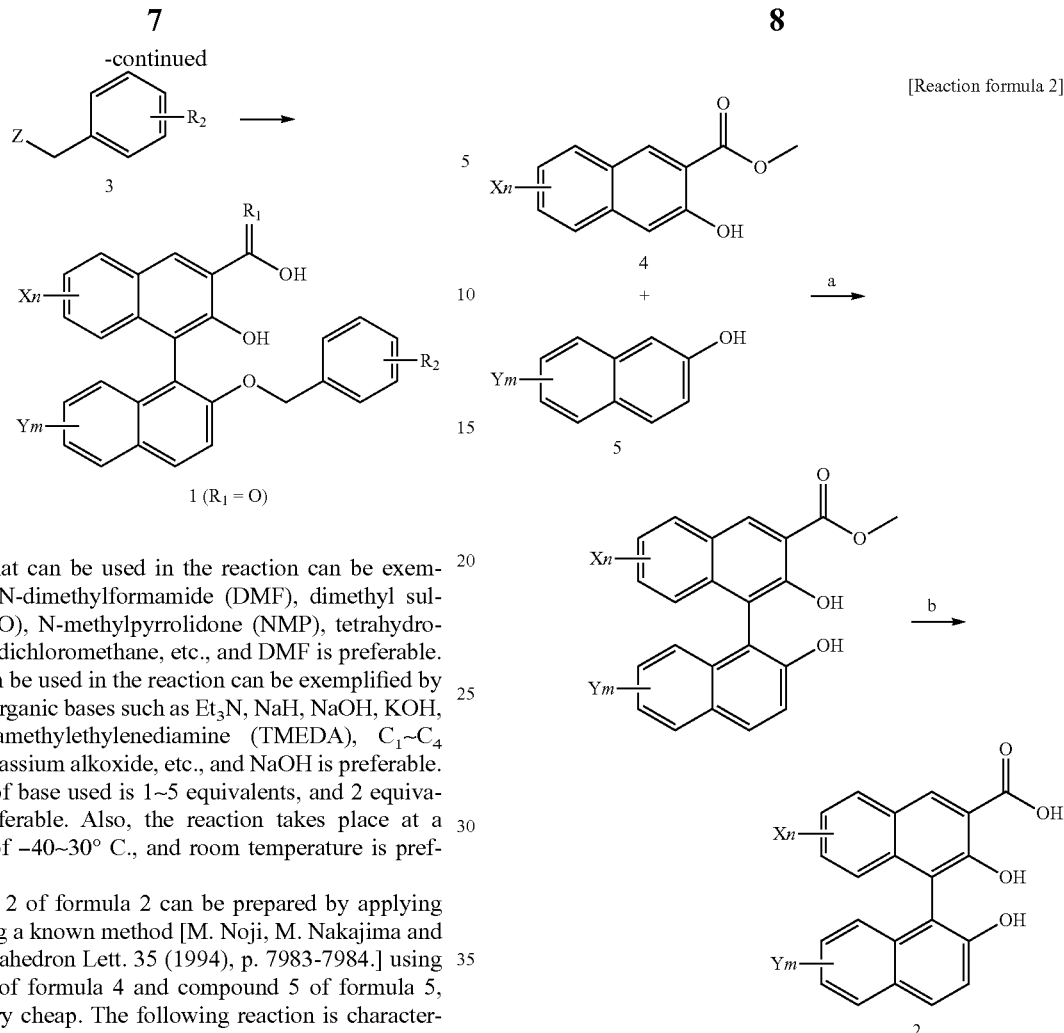

Solvents that can be used in the reaction can be exemplified by N,N-dimethylformamide (DMF), dimethyl sulfoxide (DMSO), N-methylpyrrolidone (NMP), tetrahydrofuran (THF), dichloromethane, etc., and DMF is preferable. Bases that can be used in the reaction can be exemplified by organic or inorganic bases such as $Et_3N$, NaH, NaOH, KOH, $K_2CO_3$, tetramethylethylenediamine (TMEDA), $C_1$~$C_4$ sodium or potassium alkoxide, etc., and NaOH is preferable. The amount of base used is 1~5 equivalents, and 2 equivalents are preferable. Also, the reaction takes place at a temperature of −40~30° C., and room temperature is preferable.

Compound 2 of formula 2 can be prepared by applying and improving a known method [M. Noji, M. Nakajima and K. Koga. Tetrahedron Lett. 35 (1994), p. 7983-7984.] using compound 4 of formula 4 and compound 5 of formula 5, which are very cheap. The following reaction is characterized by dissolving compound 4 into THF and adding compound 5 thereto, and adding CuCl(OH)-TMEDA to the mixed solution and carrying out the reaction in the presence of oxygen (details will be explained in example 1). Unlike the expensive binaphthol derivatives which have been used in prior art, the following compounds 4 and 5 are cheap and can be purchased in a large amount. Thus, the compound of formula 1, which is the target compound of the present invention, can be prepared economically.

[formula 4]

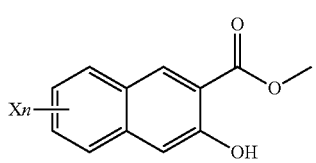

[formula 5]

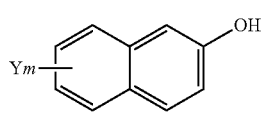

wherein X, Y, n and m are each as defined above.

The reaction formula of the method for preparing compound 2 of formula 2 is represented as follows:

Reaction a above is a reaction using CuCl(OH)-TMEDA mentioned above, and reaction b is a hydrolysis reaction of ester using a base. As the base and solvent in the reactions, any base or solvent well known in the pertinent art can be used without limit.

Reaction a and reaction b have advantages that they are both economic because they proceed almost quantitatively and they are safe because they do not have to use hazardous compounds. Thus, compound 2 of formula 2 can be prepared safely and economically by the above method.

In case where compound 2 of formula 2 is synthesized by the above reactions, a racemic mixture is obtained. Thus, it is necessary to obtain an enantiomerically pure compound 2 of formula 2 therefrom. In the present invention, there is no limitation in the method for preparing an enantiomerically pure compound 2 of formula 2. As an example, compound 2 of formula 2 can be prepared in an enantiomerically pure form by resolution using cinchonidine, by applying and improving the method disclosed by Hovorka, M. et al. (Hovorka, M.; Stibor, I.; Holakovsky, R.; Smiskova, I.; Struzka, V. Czech Rep. (2001), CZ 287879 B6).

The above exemplary method can be illustrated as the following reaction formula 3.

[Reaction formula 3]

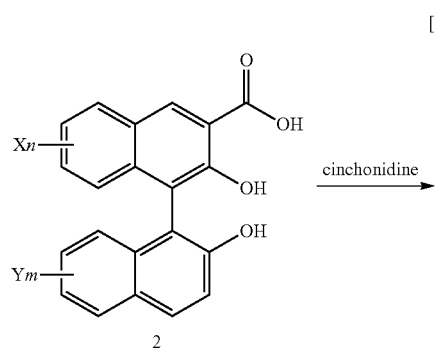

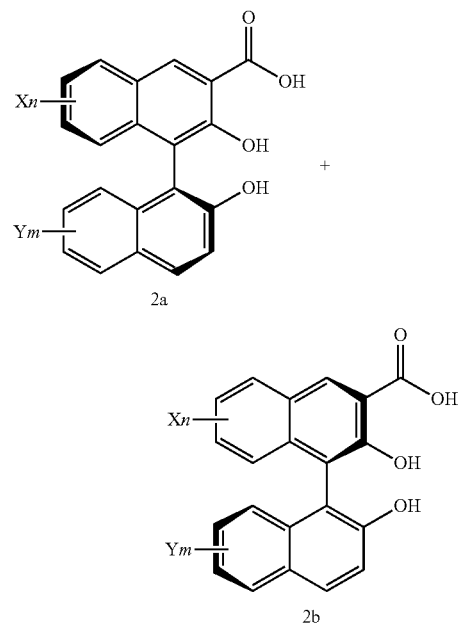

The racemic mixture can be separated into enantiomerically pure compounds 2a (S-enantiomer) and 2b (R-enantiomer) by the reaction formula above, and if a reaction is carried out according to the following reaction formula 4 using compound 2a, the target compound 1a (R₁=O) or 1a (R₁=H,H) can be prepared.

[Reaction formula 4]

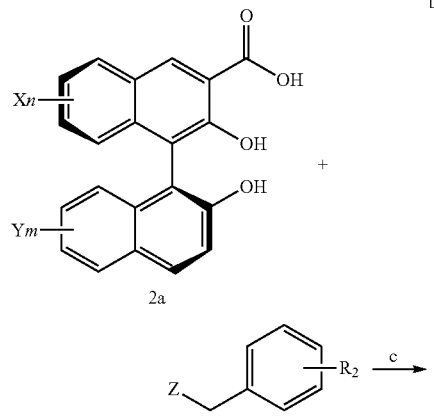

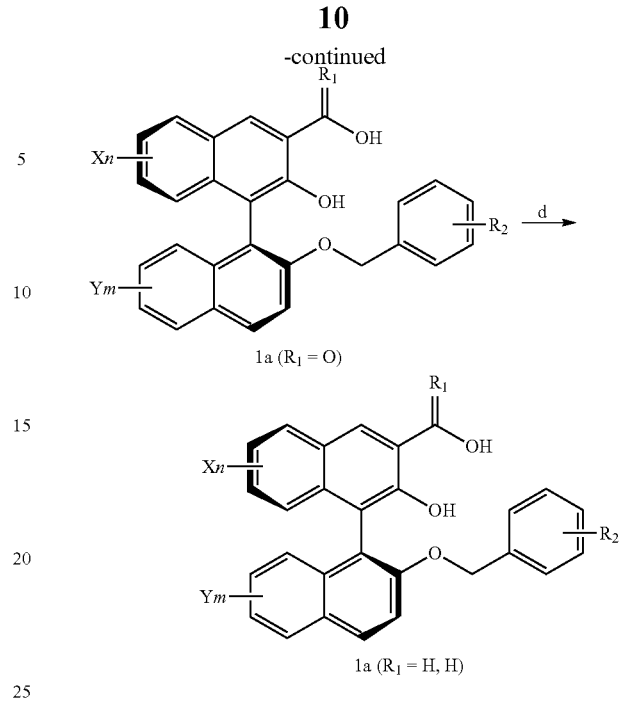

As a solvent for reaction c, as described for reaction formula 1 above, N,N-dimethylformamide (DMF), N-methyl-2-pyrrolidone (NMP), dimethyl sulfoxide (DMSO), tetrahydrofuran (THF), dichloromethane, etc. can be used, and DMF is preferable. As a base used in reaction c, organic or inorganic bases such as Et₃N, NaH, NaOH, and C₁~C₄ sodium or potassium alkoxide, etc. can be used, and NaOH is preferable. The amount of base used is 1~5 equivalents, and 2 equivalents are preferable. Also, reaction c takes place at a temperature of −40~30° C., and room temperature is preferable.

As a solvent for reaction d, tetrahydrofuran, dioxane, dichloromethane, toluene, etc. can be used, and tetrahydrofuran is preferable. As a reducing agent used in reaction d, reducing agents well known in the field can be used without limit, and a mixture of BF₃ Et₂O and sodium borohydride is preferable.

Also, the target compound 1b (R₁=O) or 1b (R₁=H,H) can be prepared by the method of reaction formula 4 using the compound 2b (R-enantiomer) obtained by reaction formula 3 as starting material.

Compound 1, 1a or 1b of formula 1 of the present invention is used as an important intermediate for preparing the compound of the following formula 6, which is very useful for separating chiral amino alcohols or amino acids into their respective optical isomers by recognizing their chirality through an imine bond or for converting L-amino acid into D-amino acid or D-amino acid into L-amino acid.

[formula 6]

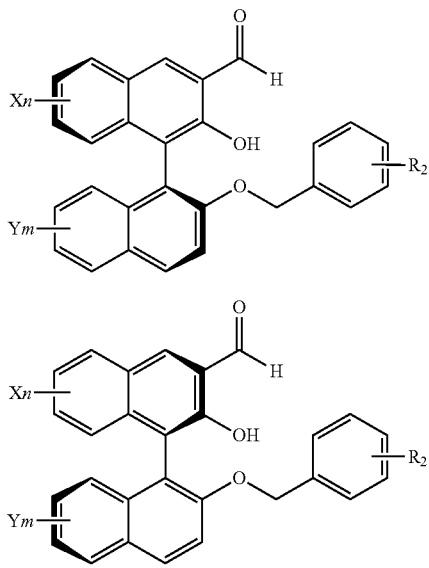

Hereinafter, the present invention is explained in more detail with reference to examples. However, the following examples are for exemplifying the present invention. Thus, the present invention is not limited to the following examples, but various modifications can be made thereto.

EXAMPLES

Example 1

Preparation of [(S)-4-(2-(3-(3-p-tolylureido)benzyloxy)naphthalene-1-yl)-3-hydroxy-2-naphthoic acid] (Compound 1a ($R_1$=O))

After dissolving (S)-3-hydroxy-4-(2-hydroxynaphthalene-1-yl)-2-naphthoic acid (9.0 g, 27 mmol) obtained by separating compounds 2 of reaction formula 2 prepared by applying and improving the known method of M. Noji, M. Nakajima and K. Koga. Tetrahedron Lett. 35 (1994), p. 7983-7984. by resolution using cinchonidine by applying and improving the technology disclosed by Hovorka, M. et al (Hovorka, M.; Stibor, I; Holakovsky, R.; Smiskova, I.; Struzka, V. Czech Rep. (2001), CZ 287879 B6) in 54 mL of DMF, 2.2 g of NaOH is added, and the mixture is stirred for 1 hour at room temperature. After adding 1-(3-(bromomethyl)phenyl)-3-p-tolylurea (8.7 g, 27 mmol) to the reaction solution, the mixture is stirred for three hours, and the solid generated by adding water is filtered to obtain 15.3 g of the subject compound (yield: 99%, purity: 96.5%).

$^1$H NMR (DMSO-$d_6$, 400 MHz), 8.60 (s, 1H, OH), 7.84 (d, 1H, ArH), 7.79 (d, 1H, ArH), 7.73 (d, 1H, ArH), 7.43 (s(br), 1H, OH), 7.33~7.24 (m, 2H, ArH), 7.22~7.17 (m, 4H, ArH), 7.13 (s(br), 1H, NH), 7.08~7.00 (m, 4H, ArH), 6.92~6.88 (m, 3H, ArH), 6.84 (s(br), 1H, NH), 6.61 (d, 1H, ArH), 4.89 (dd, 2H, $CH_2$), 2.16 (s, 3H, $CH_3$).

HPLC analysis condition: analysis instrument: HPLC (Agilent 1200 series); column: CAPCELL PAK UG120 $C_{18}$ (3.0×150 mm, Shisheido), temperature: 30° C.; solvent: 60% acetonitrile/$H_2O$ (0.1% $H_3PO_4$) (6/4, v/v), flow rate: 0.5 mL/min, detection wavelength: 230 nm Example 2

Preparation of [(S)-1-(3-((1-(2-hydroxy-3-(hydroxymethyl)naphthalene-1-yl) naphthalene-2-yloxy)methyl)phenyl)-3-p-tolylurea] (Compound 1a ($R_1$=H,H))

After dissolving the (S)-4-(2-(3-(3-p-tolylureido)benzyloxy)naphthalene-1-yl)-3-hydroxy-2-naphthoic acid (15.3 g, 27.0 mmol) obtained in example 1 in THF (150 mL), $BF_3 \cdot Et_2O$ (3.1 g) and sodium borohydride (15 g) are added sequentially. After stirring the reaction mixture at 60° C. for 8 hours, dilute hydrochloric acid is added to complete the reaction, and ethyl acetate (150 mL) and water (150 mL) are added. The subject compound is obtained by drying the organic layer with anhydrous $MgSO_4$ and filtering and condensing it (14.9 g, yield: 100%, purity: 95.5%).

$^1$H NMR (CDCl$_3$, 400 MHz), 7.91 (d, 1H, ArH), 7.81 (d, 1H, ArH), 7.71 (d, 1H, ArH), 7.68 (s, 1H, ArH), 7.63 (s, 1H, ArH), 7.48 (s, 1H, OH), 7.37 (d, 1H, ArH), 7.34~7.29 (m, 2H, ArH), 7.25~7.12 (m, 5H, ArH), 7.03~6.87 (m, 4H, ArH), 6.61~6.57 (m, 2H, ArH), 6.00 (s, 1H, NH), 5.08 (d, 1H, 1/2$CH_2OH$), 4.91 (d, 1H, 1/2$CH_2OH$), 4.73 (dd, 2H, $CH_2$), 2.25 (s, 3H, $CH_3$).

HPLC analysis condition: analysis instrument: HPLC (Agilent 1200 series); column: CAPCELL PAK UG120 $C_{18}$ (3.0×150 mm, Shisheido), temperature: 30° C.; solvent: 60% acetonitrile/$H_2O$ (0.1% $H_3PO_4$) (6/4, v/v), flow rate: 0.5 mL/min, detection wavelength: 230 nm Example 3

Preparation of [(R)-4-(2-(3-(3-p-tolylureido)benzyloxy)naphthalene-1-yl)-3-hydroxy-2-naphthoic acid] (Compound 1b ($R_1$=O))

The subject compound is obtained by the same method as example 1 using (R)-3-hydroxy-4-(2-hydroxynaphthalene-1-yl)-2-naphthoic acid.

$^1$H NMR (DMSO-$d_6$, 400 MHz), 8.61 (s, 1H, OH), 7.87 (d, 1H, ArH), 7.81 (d, 1H, ArH), 7.73 (d, 1H, ArH), 7.37~7.17 (m, 8H, ArH+NH), 7.07~6.89 (m, 9H, ArH+NH), 6.69 (d, 1H, ArH), 4.94 (dd, 2H, $CH_2$), 2.19 (s, 3H, $CH_3$)

Example 4

Preparation of [(R)-1-(3-((1-(2-hydroxy-3-(hydroxymethyl)naphthalene-1-yl)naphthalene-2-yloxy)methyl)phenyl)-3-p-tolylurea] (Compound 1b ($R_1$=H,H))

The subject compound is obtained by the same method as example 1 using (R)-4-(2-(3-(3-p-tolylureido)benzyloxy)naphthalene-1-yl)-3-hydroxy-2-naphthoic acid.

$^1$H NMR (CDCl$_3$, 400 MHz), 7.96 (d, 1H, ArH), 7.85 (d, 1H, ArH), 7.76 (d, 1H, ArH), 7.74 (s, 1H, ArH), 7.59 (s, 1H, ArH), 7.51 (d, 1H, ArH), 7.49 (d, 1H, ArH), 7.44~7.15 (m, 8H, ArH), 7.05~6.96 (m, 4H, ArH), 6.65 (d, 1H, ArH), 6.58 (s, 1H, NH), 5.19 (d, 1H, 1/2$CH_2OH$), 5.01 (d, 1H, 1/2$CH_2OH$), 4.78 (dd, 2H, $CH_2$), 2.26 (s, 3H, $CH_3$).

The invention claimed is:
1. A method for preparing the compound represented by the formula 1, comprising the step of reacting the compound represented by the formula 2 with the compound represented by the formula 3 in an organic solvent in the presence of a base;

[Formula 1]

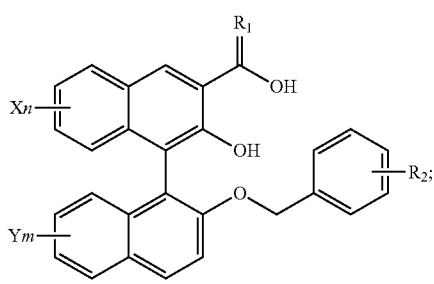

[Formula 2]

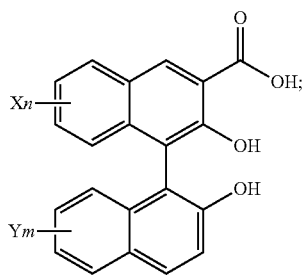

[Formula 3]

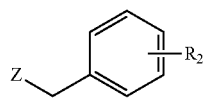

wherein
- X and Y are each independently selected from the group consisting, of hydrogen; halogen; amino; nitro; cyano; $C_1$-$C_{10}$ alkyl non-substituted or substituted with at least one substituent selected from the group consisting of halogen, hydroxyl, amino, cyano, nitro and $C_6$-$C_{10}$ aryl; $C_1$-$C_{10}$ alkyl carbonyl; $C_5$-$C_{10}$ aryl; and $C_1$-$C_{10}$ alkoxy;
- n and m are each independently an integer from 0 to 5;
- $R_1$ is oxygen;
- $R_2$ is —$NO_2$, —NH(NHBOCNBOC), —NHCX'$R_3$, —NHS(=O)$_a$$R_3$ or —NHPO(OH)$R_3$, wherein
- X' is oxygen or sulfur;
- a is 1 or 2; and
- $R_3$ is hydrogen; $C_1$-$C_{10}$ alkyl non-substituted or substituted with a halogen; —$NR_4R_5$; or $OR_6$, wherein
- $R_4$ to $R_6$ are each independently selected from the group consisting of hydrogen; $C_1$-$C_{10}$ alkyl non-substituted or substituted with a halogen; $C_5$-$C_{12}$ aryl non-substituted or substituted with at least one substituent selected from the group consisting of halogen, nitro, $C_1$-$C_5$ alkyl, $C_1$-$C_5$ alkoxy and $C_1$-$C_5$ perfluoroalkyl; and
- Z is halogen.

2. The method for preparing according to claim 1, wherein the base is an organic base which is triethylamine (TEA) or tetramethylethylenediamine (TMEDA), or an inorganic base selected from the group consisting of NaH, NaOH, KOH and $K_2CO_3$.

3. The method for preparing according to claim 1, wherein the organic solvent is selected from the group consisting of N,N-dimethylformamide, dimethylsulfoxide, N-methylpyrrolidone and tetrahydrofuran.

4. The method for preparing according to claim 1, wherein the compound represented by the formula 2 is S-enantiomer which is represented by the formula 2a, and the compound represented by the formula 1 is the S-enantiomer which is represented by the formula 1a:

[Formula 1a]

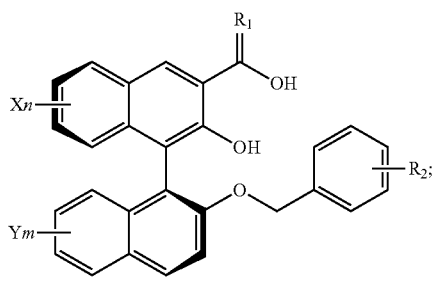

[Formula 2a]

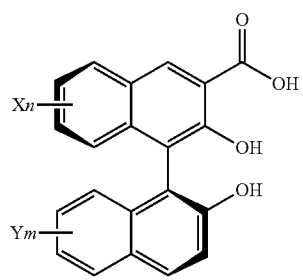

wherein X, Y, n, m, $R_1$ and $R_2$ are each as defined in claim 1.

5. The method for preparing according to claim 1, wherein the compound represented by the formula 2 is the R-enantiomer which is represented by the formula 2b, and the compound represented by the formula 1 is the R-enantiomer which is represented by the formula 1b:

[Formula 1b]

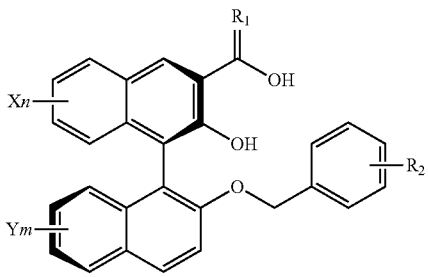

[Formula 2b]

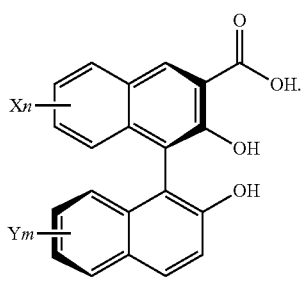

* * * * *